US009101589B2

(12) United States Patent
Funda et al.

(10) Patent No.: US 9,101,589 B2
(45) Date of Patent: Aug. 11, 2015

(54) BEADLETS COMPRISING HOP ACID SALTS IN A STARCH MATRIX

(71) Applicant: DSM IP ASSETS B.V., Heerlen (NL)

(72) Inventors: Elger Funda, Basel (CH); Dominique Joas, Basel (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/372,845

(22) PCT Filed: Dec. 28, 2012

(86) PCT No.: PCT/EP2012/077035
§ 371 (c)(1),
(2) Date: Jul. 17, 2014

(87) PCT Pub. No.: WO2013/107608
PCT Pub. Date: Jul. 25, 2013

(65) Prior Publication Data
US 2014/0363515 A1    Dec. 11, 2014

(30) Foreign Application Priority Data
Jan. 19, 2012 (EP) .................................... 12151686

(51) Int. Cl.
| A61K 9/16 | (2006.01) |
| A61K 36/00 | (2006.01) |
| B29B 9/00 | (2006.01) |
| A61K 36/185 | (2006.01) |
| A23K 1/14 | (2006.01) |
| A23K 1/16 | (2006.01) |
| A23K 1/18 | (2006.01) |
| A23L 1/00 | (2006.01) |
| C12C 3/06 | (2006.01) |
| C12C 3/08 | (2006.01) |
| A23K 1/00 | (2006.01) |
| A23L 1/30 | (2006.01) |
| A23K 1/17 | (2006.01) |
| A61K 9/50 | (2006.01) |

(52) U.S. Cl.
CPC .............. *A61K 36/185* (2013.01); *A23K 1/002* (2013.01); *A23K 1/004* (2013.01); *A23K 1/14* (2013.01); *A23K 1/1612* (2013.01); *A23K 1/1643* (2013.01); *A23K 1/17* (2013.01); *A23K 1/184* (2013.01); *A23K 1/1813* (2013.01); *A23K 1/1826* (2013.01); *A23L 1/0029* (2013.01); *A23L 1/30* (2013.01); *A61K 9/5036* (2013.01); *A61K 9/5089* (2013.01); *C12C 3/06* (2013.01); *C12C 3/08* (2013.01)

(58) Field of Classification Search
None
See application file for complete search history.

(56) References Cited

U.S. PATENT DOCUMENTS

| 5,624,701 A | 4/1997 | Maye et al. |
| 2006/0083775 A1 | 4/2006 | Rigby et al. |
| 2009/0092735 A1 | 4/2009 | Yamaguchi et al. |

FOREIGN PATENT DOCUMENTS

WO    WO 2004/026041    4/2004

OTHER PUBLICATIONS

Jafari et al.; Drying Technology, 26: 816-835 (2008).*
International Search Report for PCT/EP2012/077035, mailed Feb. 25, 2013.

* cited by examiner

*Primary Examiner* — Jeffrey T Palenik
(74) *Attorney, Agent, or Firm* — Nixon & Vanderhye P.C.

(57) ABSTRACT

The present invention relates to a process for production of beadlets comprising hop acids salts in a matrix comprising at least one starch and/or starch derivative, to such beadlets and to the use of such specific beadlets.

8 Claims, No Drawings

BEADLETS COMPRISING HOP ACID SALTS IN A STARCH MATRIX

This application is the U.S. national phase of International Application No. PCT/EP2012/077035, filed 28 Dec. 2012, which designated the U.S. and claims Priority to EP Application No. 12151686.8, filed Jan. 2012, the entire contents of each of which are incorporated herein by reference.

The present invention relates to a process for production of beadlets comprising hop acids salts in a matrix comprising at least one starch and/or starch derivative, to such beadlets and to the use of such specific beadlets.

Hop acids are used in farm animals to improve overall animal performance since they act in the digestive system of the animal as mild antibiotics or ionophores (WO2010/123571). Hop acids include but are not limited to alpha acids, beta acids and their isomerized forms. Beta acids include lupulone, colupulone, adlupulone as well as other analogs. Alpha acids include humulone, cohumulone, adhumulone, posthumulone, prehumulone, as well as other analogs.

The knowledge of the antimicrobial properties of the hop acids dates back a very long time, and the benefit of natural antimicrobial to the growth and health performance of farm animals in industrial production is also undisputed and their safety to consumption is also very well documented in the art. However, the use of hop acids in animal feeding is practically not possible in the industry because of the instability of the compounds when exposed to air and humidity in the feed.

Therefore, there is a need in the industry to provide stabilized forms of hop acids and hop extracts which are resistant to moisture and oxygen during storage, when used in a feed or a feed premix, moreover, hop acids should also be stable when subjecting the feed containing hop acids to the harsh conditions of feed pelleting at high temperature which is a standard in the swine and broiler feed industry.

A very typical form of formulation of substances used in consumer products (such as for example food products) are powders. Powders can be produced by spray drying or spray granulation processes but they do not allow stabilisation of hop acids such that they are not degraded in the feed or feed premix.

Another well known form of preparations are beadlets. Beadlets provide superior handling properties in that they are not dusty and possess good flowablity characteristics. Beadlets are solely known for fat-soluble substances.

Beadlets (comprising fat-soluble substances) and their methods of productions are known from the prior art. These beadlets comprise fat-soluble (lipophilic, hydrophobic) substances. Such beadlets and their process for production are for example known from US2006/0115534 and U.S. Pat. No. 4,670,247. These beadlets usually have good storage stability, but the production of such beadlets requires an emulsification or dispersion step to distribute the water-insoluble active in the aqueous matrix phase. Therefore, the matrix material needs to have emulsifying properties or an additional emulsifier is required.

The goal of the present invention was to find a process for producing formulations comprising hop acids, which allows producing storage stable and pelleting stable formulations using a simple process and that can be produced at a cost compatible with the feed and feed additive industry.

Surprisingly, it has been found that using hop acids in their deprotonated form at high pH allows their formulation in the powder catch process without the need for an emulsification step. The formulations are in the form of beadlets having the above mentioned advantages. The beadlets comprise one or more hop acids salts and one starch and/or starch derivative (or a mixture of starches and/or starch derivatives) as a matrix material. Furthermore these beadlets can be coated with a layer of the powder catch medium.

Therefore, the present invention relates to a process for preparing beadlets, which comprise at least one hop acid salt, comprising:
(a) forming an aqueous solution of
  (i) at least one hop acid salt and
  (ii) at least one starch and/or at least one starch derivative,
(b) adjusting the pH of the solution to pH greater than 9
(c) converting the solution into a dry powder by spray drying into a starch collecting powder.

The aqueous solution is preferably adjusted to a pH greater than 9, more preferably greater than 9.5 in order to prevent the precipitation of hop acid salts.

Such a process is known from the prior art. It can be found for example in U.S. Pat. No. 6,444,227 or WO04062382.

Preferred hop acids according to the present invention include but are not limited to alpha acids, beta acids and their isomerized forms. Beta acids include lupulone, colupulone, adlupulone as well as other analogs and mixtures thereof. Alpha acids include humulone, cohumulone, adhumulone, posthumulone, prehumulone, as well as other analogs and mixtures thereof.

Hop acid salts include metal salts like sodium or potassium or alkaline earth metal salts like calcium and magnesium. Preferred salts for all embodiments of the present invention are potassium salts, and preferred hop acids are beta acids.

Therefore a preferred embodiment of the present invention relates to a process for preparing beadlets, which comprise at least one hop beta acid salt. More preferred hop acid salt is a mixture of hop beta acid salts primarily comprising lupulone, colupulone, and adlupulone salts. More preferred salt is potassium salt.

The hop acids are formulated in a beadlet by a matrix material, which comprises at least one starch and/or starch derivative.

Starch having the chemical formula $(C_6H_{10}O_5)_n$ is a polysaccharide carbohydrate consisting of a large number of glucose monosaccharide units joined together by glycosidic bonds.

All plant seeds and tubers contain starch. Starches are commonly extracted from plants, such as corn, sorghum, wheat, rice, tapioca, arrowroot, sago, potato, quinoa and amaranth.

Natural starches contain usually amylase and amylopectin molecules. The content of amylase in natural starches can vary from 0 wt-% (for example waxy corn starch and waxy rice starch) up to about 85wt-% (High amylase corn starch). Normal starches contain about 25 wt-% of amylase. As a consequence thereof the content of amylopectin is between 15 and 100 wt-%.

It is also possible to use starch derivatives (modified starches) including hydrolysed starches. The starches can be modified in various manners. It can be done physically and chemically.

Pregelatinised starches are examples of physically modified starches.

Acidic modified, oxidized, cross-linked, starch esters, starch ethers and cationic starches are examples of chemically modified starches. Important examples of such modified starches are octenyl succinic anhydride starches (OSA starches).

Dextrins like maltodextrin or yellow dextrin are examples of starch derivatives obtained by partial hydrolysis.

In a preferred process according to the present invention the starches or starch derivatives are chosen from the group consisting of amylopectin, maltodextrin, yellow dextrins and pregelatinised starches. Even more preferred starch is maltodextrin.

The matrix of the beadlets of the present invention can also comprise additional compounds, such as sugar. Sugar refers to any monosaccharide or disaccharide (preferred is sucrose).

The matrix of the beadlets may also comprise further excipients, such as plasticizers or antioxidants (e.g. EMQ).

A preferred process according to the present invention is a powder catch process. Such a process is known from the prior art (for example from WO04062382). As a result of such a powder catch process the beadlets are covered by a layer of the powder.

Therefore, the beadlets produced according to this process are preferably covered by a layer of the powder catch medium. This layer (coating) is in the form of a powder coating. The powder catch medium is a compound (or a mixture of compounds), which is able to absorb moisture and to form a powder coating. Suitable powder catch media are i.e. starches, silicate or phosphate compounds. Preferred powder catch media are starches (such as i.e. corn starch), calcium silicate, calcium aluminium silicate and tri-calcium phosphate. Most preferred are starches, especially corn starch.

Beadlets are a well known form of formulation for fat-soluble substances. An important advantage of the generally spherical beadlets is that they are not dusty and that they show excellent free flowing characteristics, which are very desirable for manufacturing and formulating operations.

Usually the size of a beadlet is from 5 μm to 1,000 μm (preferably from 250 μm to 850 μm). The sizes can be smaller or larger. The size of a beadlet can be determined according to well known methods, such as (scanning) electron microscopy.

A suitable method to produce beadlets as disclosed and described above is for example described in WO 2004/062382.

The process according to the present invention surprisingly allows producing beadlets with a high stability of hop acid salts in the product itself and when mixed with a feed premix or with feed, with good overall properties and without requiring an emulsification step.

The process as described in the present patent application can be used to produce beadlets with an amount of hop acid salts adjusted to the needs of the feed industry. The amount can be as low as 5 wt-%, based on the total weight of the beadlets, Usually the content of hop acid salts in the beadlets is comprised between 5 wt-% and 25 wt-%, preferably between 10 wt-% and 15 wt-%, based on the total weight of the beadlets.

A preferred process according to present invention relates to a process as described above wherein the beadlets comprise 5 wt-% to 25 wt-%, based on the total weight of the beadlets, of at least one hop acid salt, preferably between 10 wt-% and 15 wt-%, based on the total weight of the beadlets.

A preferred process according to present invention relates to a process wherein the beadlets comprise at least 30 wt-%, based on the total weight of the beadlets, more preferred at least 50 wt-%, of at least one starch and/or at least one starch derivative (matrix material) and of the powder coating layer.

A preferred process according to present invention relates to a process wherein the beadlets comprise at least 3 wt-%, based on the total weight of the beadlets, of powder coating layer.

A more preferred process according to present invention relates to a process wherein the beadlets comprise
(i) 5 wt-% to 25 wt-%, preferably 10 wt-% to 20 wt-%, more preferably 10 wt-% to 15 wt-%, based on the total weight of the beadlets, of at least one hop acid salt, and
(ii) 30 wt-% to 90 wt-%, preferably 50 wt-% to 85 wt-%, based on the total weight of the beadlets, of at least one starch and/or at least one starch derivative, and
(iii) 3 wt-% to 50 wt-%, preferably 5 wt-% to 20 wt-%, based on the total weight of the beadlets, of starch powder coating.

Another embodiment of the present invention relates to a process, wherein the starch component (ii), always comprise maltodextrin and at least one further starch and/or at least one further starch derivative.

The matrix of the beadlets of the present invention as described above can also comprise additional compounds. Such compounds can be any kind of auxiliaries used in the field of beadlet producing and/or feed technology. A preferred compound is sugar (sucrose). A preferred antioxidant is EMQ.

Beadlets comprising a high amount (up to 25 wt-%) of hop acid salts in a matrix comprising at least one starch and/or at least one starch derivative are not known from the prior art.

A further embodiment of the present invention relates to beadlets (B1) comprising
(i) 5 wt-% to 25 wt-%, based on the total weight of the beadlets, of at least one hop acid salt and
(ii) at least one starch and/or starch derivative.

The invention also relates to beadlets (B2) comprising
(i) 10 wt-% to 15 wt-%, based on the total weight of the beadlets, of at least one hop acid salt, and
(ii) at least one starch and/or starch derivative.

Preferred beadlets (B1') according to present invention comprise
(i) 5 wt-% to 25 wt-%, based on the total weight of the beadlets, of at least one hop acid salt and
(ii) at least 30 wt-%, based on the total weight of the beadlets, of at least one starch and/or starch derivative.

The beadlets (B2') comprise
(i) 10 wt-% to 15 wt-%, based on the total weight of the beadlets, of at least one hop acid salt, and
(ii) at least 50 wt-%, based on the total weight of the beadlets, of at least one starch and/or at least one starch derivative.

Preferred starch covered beadlets according to present invention comprise at least 3 wt-%, based on the total weight of the beadlets, of the powder coating layer.

Therefore (B1), (B1'), (B2) and (B2') preferably comprise at least 5 wt-%, based on the total weight of the beadlets, of starch powder coating layer.

More preferred beadlets according to the present invention (B3) comprise
(i) 5 wt-% to 25 wt-%, preferably 10 wt-% to 15 wt-%, based on the total weight of the beadlets, of at least one hop acid salt, and
(ii) 30 wt-% to 90 wt-%, preferably 50 wt-% to 85 wt-%, based on the total weight of the beadlets, of at least one starch and/or starch derivative chosen from the groups consisting of corn starch, sorghum starch, wheat starch, rice starch, tapioca starch, arrowroot starch, sago starch, potato starch, quinoa starch and amaranth starch, pregelatinised starches, acidic modified starches, oxidized starches, cross-linked starches, starch esters, starch ethers, dextrins and cationic starches (preferred are starches with a high amount of amylopectin, OSA starches, maltodextrins, yellow dextrins and pregelatinised starches, and (iii) 3 wt-% to 50 wt-%, preferably 5 wt-% to 20 wt-%, based on the total weight of the beadlets, of starch powder coating.

Further, more preferred beadlets are beadlets (B1), (B1'), (B2), (B2'), and (B3) additionally comprising sugar (sucrose). These beadlets (B4) comprise 5-25 wt-%, preferably 10-20 wt-%, based on the total weight of the beadlets, of sucrose.

An especially preferred embodiment of the present invention are beadlets (B5) which comprise a mixture of maltodextrin and at least one further starch and/or starch derivative in the matrix. Therefore a further embodiment of the present invention relates to beadlets (B1), (B1'), (B2), (B2'), (B3), and (B4), in which the starch component (ii) comprises maltodextrin and at least one further starch and/or starch derivative.

A further embodiment according to the present invention relates to the use of the beadlets (B1), (B1'), (B2), (B2'), (B3), (B4), and (B5) in feed products as well in the production of feed products.

Feed products in the context of the present invention comprise liquid and solid feed products as well as paste-like and or gel like. The feed products comprise feed for animals (especially ruminants, poultry and swine).

Suitable animal feed products can be in any commonly used form.

Therefore a further embodiment of the present invention relates to animal feed products and to animal feed additives comprising beadlets as described above.

Premixes are a convenient usage form for the feed producers but are a critical medium for various ingredients due to pH, ionic strength and water activity values, which can negatively affect stability of various ingredients. But the beadlets according to the present invention eliminate (or at least strongly minimize) such problems.

The beadlets according to the present invention can also be used in premixes for feed products.

A further embodiment of the present invention is a premix for feed products comprising beadlets according to the present invention.

Functional ingredients like vitamins and trace elements are often added to feed products as well as to premixes.

The following examples serve to illustrate the invention. The percentages are expressed in weight percentages and the temperatures are degrees Celsius, if not otherwise defined.

EXAMPLE 1

Formulation of Potassium Salts of Hop Beta Acid in a Matrix Comprising Maltodextrin 30 g hop acids extract potassium salts (54.4% beta acids) and 40 g maltodextrin MD01 were dissolved in 60 g water with stirring, and pH adjusted to 9. About 100 g of the solution was sprayed in a spraying pan in a bed of fluidized starch at about 25° C. by means of a rotating spraying nozzle. The so-obtained beadlets were separated from excess starch by sieving and dried with a fluid bed drier. There were obtained ca. 130 g of dry powder having a beta acids content of 19.7 wt-%.

A comparative formulation of hop beta acid potassium salts by spray granulation has also been performed in a matrix comprising maltodextrin:

70 g hop acids extract potassium salts (54.4% beta acids) and 35 g maltodextrin MD01 were dissolved in 100 g water with stirring. The solution was sprayed on 150 g microcyrstalline cellulose in a fluid-bed processor (Wurster process) at a product temperature of 50-55° C. There were obtained ca. 180 g of dry powder having a beta acids content of 11.9 wt-%.

EXAMPLE 2

Stability of Hop Acid Beadlets According to the Present Invention in Comparison to Spray Granulates of Example 1

Products from example 1 were stored for 1 week and up to 4 months at 25° C. Stability was measured as recovery of beta acids content compared to initial. Results are shown in the table 1 below. As can be seen from the table, stability of the beadlet form much more stable than a comparable spray granulate.

TABLE 1

Recovery of hop beta acids following storage at 25° C.

| Sample | recovery after 1 week | recovery after 4 months |
| --- | --- | --- |
| Beadlet of example 1 | 95% | 82% |
| Spray granulate of example 1 | 77% | 35% |

EXAMPLE 3

Formulation of Potassium Salts of Hop Beta Acid in a Matrix Comprising Maltodextrin 200 g hop acids extract potassium salts (53.2% beta acids) and 320 g maltodextrin MD01 were dissolved in 500 g water with stirring and pH adjusted to 9. The solution was sprayed in a spraying pan in a bed of fluidized starch at about 25° C. by means of a rotating spraying nozzle. The so-obtained beadlets were separated from excess starch by sieving and dried with a fluid bed drier. There were obtained ca. 1300 g of dry powder having a beta acids content of 15.96 wt-%.

EXAMPLE 4

Stability of Hop Acid Beadlets as Such and in Feed Mash

Product from example 3 was stored for up to 6 months in aluminium bags at 25° C. Stability was measured as recovery of beta acids content compared to initial. Results are shown in table 2 below. As can be seen from the table, beta acids are fully stable for at least 6 months.

TABLE 2

Recovery of hop beta acids following storage at 25° C.

| Time | Beta acids content |
| --- | --- |
| 0 months | 15.96% |
| 1 month | 15.36% |
| 2 months | 14.69% |
| 3 months | 15.19% |
| 6 months | 17.09% |

Product from example 3 was mixed into a poultry feed mash at a target concentration of 100 ppm beta acids. Mash feed was stored for 1 month at 25° C., 60% rh. Recovery of beta acids vs. initial after 1 month was 86%

The invention claimed is:

1. A process for preparing beadlets, which comprise at least one hop acid salt, comprising:
   (a) forming an aqueous solution of:
      (i) at least a hop acid salt, and
      (ii) at least one starch and/or starch derivative,
   (b) adjusting the pH of the solution to pH greater than 9, and
   (c) converting the solution into a dry powder by spray drying into a starch collecting powder, wherein
   the beadlets comprise at least 3 wt-%, based on the total weight of the beadlets, of the starch collecting powder as a coating layer.

2. The process according to claim 1, wherein the hop acid salt is a mixture comprising a lupulone salt, a colupulone salt, and an adlupulone salt.

3. The process according to claim 1, wherein the hop acid salt is a potassium salt.

4. The process according to claim 1, wherein the starch and/or starch derivatives are selected from the group consisting of amylopectin, maltodextrins, yellow dextrins and pregelatinised starches.

5. The process according to claim 1, wherein the starch and/or starch derivatives comprise maltodextrins and at least one further starch.

6. The process according to claim 1, wherein the beadlets comprise 5 to 25 wt. %, based on the total weight of the beadlets, of at least one hop acid salt.

7. The process according to claim 1, wherein the beadlets comprise at least 30 wt. %, based on the total weight of the beadlets, of the at least one starch and/or at least one starch derivative and of the starch powder coating layer.

8. The process according to claim 7, wherein the beadlets comprise at least 50 wt. % of the at least one starch and/or at least one starch derivative and of the starch powder coating layer.

* * * * *